United States Patent [19]

Gluckman

[11] 4,312,886
[45] Jan. 26, 1982

[54] PREVENTION OF GASTRIC ULCERS AND DEPRESSION OF GASTRIC SECRETION BY ADMINISTRATION OF GUANABENZ

[75] Inventor: Melvyn I. Gluckman, Ann Arbor, Mich.

[73] Assignee: American Home Products Corporation, New York, N.Y.

[21] Appl. No.: 44,837

[22] Filed: Jun. 1, 1979

Related U.S. Application Data

[63] Continuation of Ser. No. 926,486, Jul. 20, 1978, abandoned.

[51] Int. Cl.$^3$ .......................................... A61K 31/155
[52] U.S. Cl. ................................................... 424/326
[58] Field of Search .......................................... 424/326

[56] References Cited

U.S. PATENT DOCUMENTS

| 3,591,636 | 7/1971 | Houlihan et al. | 260/564 |
| 3,592,935 | 7/1971 | Houlihan et al. | 424/326 |
| 3,658,993 | 4/1972 | Kodama et al. | 424/326 |
| 3,880,043 | 3/1974 | Douglas et al. | 424/326 |
| 4,006,249 | 6/1976 | Porter et al. | 424/326 |
| 4,006,250 | 2/1977 | Childress | 424/326 |
| 4,060,640 | 11/1977 | Kodama et al. | 424/326 |

FOREIGN PATENT DOCUMENTS 1019120  2/1966  United Kingdom ................ 424/326

OTHER PUBLICATIONS

Hanson et al.–*J. Appl. Physiol.*, 15, 291–294 (1960).
Drugs of Choice–1976–1977–The C. V. Mosby Co., pp. 326–333.
*Gastroenterology*, 26, 906 (1954).
*Br. J. Pharmacol.*, 41, 161 (1971); 58 419 (1976).
*Journal of Med. Chem.*, 1975, vol. 18, No. 1, 90–99.

*Primary Examiner*—Frederick E. Waddell
*Attorney, Agent, or Firm*—George Tarnowski

[57] ABSTRACT

Methods for the prevention of ulcer formation and for the depression of gastric secretions by the administration of guanabenz are disclosed.

2 Claims, No Drawings

PREVENTION OF GASTRIC ULCERS AND DEPRESSION OF GASTRIC SECRETION BY ADMINISTRATION OF GUANABENZ

This is a continuation of application Ser. No. 926,486, filed July 20, 1978, now abandoned.

Various drugs are employed for the treatment of peptic ulcers and/or gastric hyperacidity. (See *Drugs of Choice*, 1976–1977, Walter Modell, Editor, C. V. Mosby, Co., St. Louis, pages 328 to 332). Such drugs are either antacids which act by neutralization of gastric acidity or antisecretory agents which act by the depression of gastric secretions. The present invention relates to methods for preventing peptic ulcer formation and for depressing gastric secretions in warm-blooded animals by the administration of the chemical compound guanabenz.

Guanabenz is the generic name for the compound [(2,6-dichlorobenzylidine)amino]guanidine. The compound is described in the literature and is known to possess various biological activities. Hypotensive effects, CNS depressant effects, and psychic depressant effects are described in U.S. Pat. No. 3,659,993. The anti-inflammatory activity of guanabenz is disclosed in U.S. Pat. No. 3,592,935. The use of guanabenz for the systemic treatment of psoriasis is described in U.S. Pat. No. 4,006,249. The herbicidal properties of guanabenz are discussed in U.K. Pat. No. 1,019,120. The derivatives of guanabenz having a hydroxyl group in place of hydrogen on the terminal nitrogen also have hypotensive activity (U.S. Pat. No. 3,591,636) and antipsoriasis activity (U.S. Pat. No. 4,006,250).

Guanabenz is currently undergoing clinical trial as an antihypertensive agent. The clinical studies have shown that guanabenz in doses of 4 to 48 mg. b.i.d. can produce safe and effective lowering of blood pressure in hypertensive patients. The most frequent side effects noted were sedation and dry mouth. Two mechanisms have been proposed for the antihypertensive effects: (a) central inhibition of sympathetic impulses to the vasculature and the heart, or (b) peripheral adrenergic neuron blockage. Most data indicate that guanabenz exerts its anti-hypertensive effect largely through central pathways and only to a lesser extent through blockade of peripheral adrenergic neurons.

Clonidine is a centrally acting anti-hypertensive agent which, depending upon the test utilized, has been found either to stimulate or to inhibit gastric secretions. [See *Brit. J. Pharmacol.*, 58, 419 (1976) and the references cited therein.] Other cyclic amidines similar to clonidine have been reported to produce both antihypertensive and gastric anti-secretory effects [T. Jen et al., *J. Med. Chem.*, 18, 90 (1975)]. Aminoguanidine itself does not effect gastric hypersecretion or ulceration in rats subjected to pyloris ligation [A. West et al., *Brit. J. Pharmacol.*, 41, 16 (1971)].

In accordance with this invention, there is provided: (a) a method for preventing gastric ulcer formation in a warm-blooded animal which comprises administering to said animal in need thereof an effective amount of guanabenz, or a non-toxic pharmaceutically acceptable acid addition salt thereof; and (b) a method for depressing gastric secretion in warm-blooded animals which comprises administering to said animal in need thereof an effective amount of guanabenz or a non-toxic pharmaceutically acceptable acid addition salt thereof.

The gastric anti-ulcer activity and the gastric anti-secretory activity of guanabenz are indicated by evaluation in standard laboratory tests. Gastric anti-ulcer activity is demonstrated by the ability of guanabenz to inhibit cold restraint stress-induced ulcer formation when administered to rats [Brodie et al., *J. Appl. Physiol.*, 15, 291 (1960)]. Gastric anti-secretory activity is demonstrated by the ability of guanabenz to lower gastric volume, hydrogen ion concentration, and/or total hydrogen ion secreted in pylorous-ligated rats [see Shay et al., *Gastroenterology*, 26, 906 (1954)].

The dosage of guanabenz for preventing ulcer formation or for depressing gastric secretions will vary according to the severity and nature of the condition and the particular subject being treated. Therapy should be initiated at a dosage low enough to produce the desired anti-ulcer effect or anti-secretory effect without causing any unacceptable side effects. In general, an initial dosage of about 0.1 mg. to about 5.0 mg. per kilogram of body weight should be employed. Guanabenz can be administered daily either in a single dose or in divided doses.

When employed for the therapeutic purposes herein described, guanabenz may be administered to the subject alone or in combination with conventional pharmaceutical carriers in a wide variety of dosage forms. The nature and proportions of such carriers will be apparent to those skilled in the art. For example, guanabenz may be administered orally in solid dosage forms, such as capsules, tablets, or powders, or in liquid forms, such as solutions or suspensions. The compound may also be injected parenterally in the form of sterile solutions or suspensions. Solid oral forms may contain conventional pharmaceutically acceptable carriers, such as diluents, lubricants, stabilizers, binders, or tablet-disintegrating agents. Suitable solid carriers are starch, magnesium stearate, magnesium carbonate, talc, lactose, succose, gelatin, various resins, and like materials. Liquid oral forms include solutions, suspensions, or emulsions which may contain various conventional flavoring, preserving, stabilizing, solubilizing, or suspending agents. Parenteral preparations are sterile aqueous or non-aqueous solutions or suspensions which may contain various preserving, stabilizing, buffering, solubilizing, or suspending agents. If desired, additives, such as saline or glucose may be added to make the solution isotonic.

If desired, guanabenz may be administered in the form of an acid addition salt formed from a non-toxic pharmaceutically acceptable organic or inorganic acid. Such salts are prepared by methods well known in the art. Appropriate salts are those formed from the following acids: hydrochloric, hydrobromic, sulfuric, nitric, phosphoric, lactic, fumaric, tartaric, citric, formic, acetic, glycollic, succinic, gluconic, glutaric, and maleic.

The following Examples illustrate the methods of the invention:

EXAMPLE 1

The anti-ulcer effect of guanabenz is demonstrated and elicited by the following test procedure:

Male rats weighing between 120–160 gm. are deprived of food for 18 hours with water ad lib. The rats are divided into groups of ten and dosed by the oral route with guanabenz or vehicle control, 1.0% methylcellulose, in a volume of 5 ml/kg. Immediately after dosing, the animals are inserted into aluminum restraining tubes measuring 1⅝ inches in diameter by 8 inches and placed in the cold (4°±1° C.). The time in the cold is adjusted so that 90% of the control animals exhibit ulcers. At the end of the test period the animals are killed, the duodenum and esophagus ligated, and the stomach removed. The stomachs are inflated with water, opened along the lesser curvature, spread over the index finger, and the mucosa is gently wiped. The number of hemorrhage sites in the mucosa are counted by visual observation and recorded; however, since these numbers are so variable, only the incidence of ulcer (i.e., the number of rats with ulcers) are used for evaluation.

The percent prevention of ulcer formation is calculated as follows:

$$\frac{\text{No. rats with ulcers in control} - \text{No. rats with ulcers in treatment}}{\text{No. rats with ulcers in control}} \times 100$$

When tested according to the above-described procedure, guanabenz gave the results set forth below:

| Dose, mg/kg (base) | % Prevention |
|---|---|
| 2.5 | 0 |
| 5.0 | 50 |
| 10.0 | 70 |

EXAMPLE 2

The gastric anti-secretory effect of guanabenz is demonstrated by the following test procedure:

Male rats weighing between 200–300 gm. are fasted for 24 hours. The rats are then anesthetized with diethyl ether, weighed, and the pylorus ligated (method of Shay). Guanabenz, suspended in 1% methylcellulose (100 cps.) is administered directly in the duodenum at the time of ligation. Four hours after ligation, the rats are killed by asphyxiation with $CO_2$, the stomachs are removed, and the contents collected. The gastric juice is then centrifuged and the volume is measured. However, any samples obviously contaminated by feces, food, or other material are discarded. A 1 ml. aliquot of the gastric juice is titrated to an end point of pH 7.4 with 0.1 N NaOH. The following parameters are recorded: gastric volume, hydrogen ion, concentration, and total hydrogen ion secreted. The data are statistically compared to controls using a t-test or analysis of variance. A significant reduction ($p < 0.05$) in total acid output (mEq/4 hrs.) indicates gastric antisecretory activity of the test compound. The reduction in total acid output is expressed as a percentage decrease in total acid output relative to control values as follows:

$$\frac{\text{Control } (m\text{EqH}^+/4\text{hrs.}) - \text{Treatment } (m\text{Eq}/4\text{hrs.})}{\text{Control } (m\text{Eq}/4\text{hrs.})} \times 100 = \% \text{ Decrease}$$

When tested as described above, guanabenz showed gastric antisecretory activity as follows:

| Dose (mg/kg) | % Decrease |
|---|---|
| 2.0 | 96* |
| 1.0 | 92* |
| 0.5 | 75* |
| 0.4 | 73* |
| 0.25 | 30 |
| 0.2 | 9 |
| 0.1 | 0 |

*Indicates a statistically significant reduction in Total Acid Output.

What is claimed is:

1. A method for preventing gastric ulcer formation in a warm-blooded animal which comprises administering to said animal in need thereof an effective amount of guanabenz, or a non-toxic pharmaceutically acceptable acid addition salt thereof.

2. A method for depressing gastric secretions in a warm-blooded animal which comprises administering to said animal in need thereof an effective amount of guanabenz, or a non-toxic pharmaceutically acceptable acid addition salt thereof.

* * * * *